United States Patent
Levy (10) Patent No.: US 11,272,842 B2
(45) Date of Patent: Mar. 15, 2022

(54) SYSTEMS AND METHODS FOR ENSURING COHERENCE BETWEEN MULTIPLE ULTRASOUND TRANSDUCER ARRAYS

(71) Applicant: INSIGHTEC, LTD., Tirat Carmel (IL)

(72) Inventor: Yoav Levy, Hinanit (IL)

(73) Assignee: INSIGHTEC, LTD., Tirat Carmel (IL)

( * ) Notice: Subject to any disclaimer, the term of this patent is extended or adjusted under 35 U.S.C. 154(b) by 390 days.

(21) Appl. No.: 16/314,092

(22) PCT Filed: Jun. 20, 2017

(86) PCT No.: PCT/IB2017/000904
§ 371 (c)(1),
(2) Date: Dec. 28, 2018

(87) PCT Pub. No.: WO2018/007868
PCT Pub. Date: Jan. 11, 2018

(65) Prior Publication Data
US 2020/0178803 A1    Jun. 11, 2020

Related U.S. Application Data

(60) Provisional application No. 62/359,922, filed on Jul. 8, 2016.

(51) Int. Cl.
*A61B 5/00* (2006.01)
*A61N 7/00* (2006.01)
(Continued)

(52) U.S. Cl.
CPC ............ *A61B 5/0036* (2018.08); *A61B 5/055* (2013.01); *A61N 7/00* (2013.01); *G01R 33/4814* (2013.01);
(Continued)

(58) Field of Classification Search
CPC .... A61N 2007/0078; A61N 7/00; A61B 8/00; A61B 6/547; A61B 2034/2051;
(Continued)

(56) References Cited

U.S. PATENT DOCUMENTS

| 2005/0124897 A1* | 6/2005 | Chopra | A61B 8/0808 |
| | | | 600/459 |
| 2008/0146937 A1* | 6/2008 | Lee | A61B 8/12 |
| | | | 600/462 |

(Continued)

FOREIGN PATENT DOCUMENTS

JP    2006130313 A    5/2006

OTHER PUBLICATIONS

International Search Report and Written Opinion for International Application No. PCT/IB2017/000904, dated Nov. 11, 2017, 3 pages.

*Primary Examiner* — Christopher Koharski
*Assistant Examiner* — Andrew W Begeman
(74) *Attorney, Agent, or Firm* — Morgan, Lewis & Bockius LLP (57) ABSTRACT

A system for maintaining coherence of ultrasound waves emitted by multiple transducer arrays includes multiple retention arms, each for receiving one of the transducer arrays; a connecting frame for receiving and mechanically retaining the arms in fixed angular relation to each other; and a processor configured to determine relative locations of the transducer arrays with respect to one another and the connecting frame; determine a location of the connecting frame relative to an anatomic region of interest; determine a spatial arrangement of the transducer elements in each transducer array with respect to the anatomic region of interest; and adjust a transmission configuration of the transducer elements in the transducer arrays to achieve a desired focusing (Continued)

property with respect to the anatomic region of interest while maintaining coherence therebetween.

14 Claims, 4 Drawing Sheets

(51) Int. Cl.
*A61B 5/055* (2006.01)
*A61B 34/20* (2016.01)
*G01R 33/48* (2006.01)
*A61B 90/00* (2016.01)
*A61B 8/00* (2006.01)
*G10K 11/35* (2006.01)

(52) U.S. Cl.
CPC ..... *A61B 8/4263* (2013.01); *A61B 2034/2051* (2016.02); *A61B 2090/374* (2016.02); *A61N 2007/0078* (2013.01)

(58) Field of Classification Search
CPC ................. A61B 5/055; A61B 8/4477; A61B 8/4245–4263; A61B 8/4209–4218; A61B 2090/3983

See application file for complete search history.

(56) References Cited

U.S. PATENT DOCUMENTS

| | | | |
|---|---|---|---|
| 2009/0024034 A1* | 1/2009 | Moreau-Gobard | A61B 8/483 600/443 |
| 2009/0163910 A1* | 6/2009 | Sliwa | A61B 8/4209 606/41 |
| 2011/0034800 A1* | 2/2011 | Vitek | A61B 5/055 600/411 |
| 2011/0125022 A1* | 5/2011 | Lazebnik | A61B 8/5253 600/444 |
| 2011/0270075 A1 | 11/2011 | Vitek et al. | |
| 2016/0033601 A1 | 2/2016 | Assif | |
| 2016/0051223 A1* | 2/2016 | Kim | A61B 8/15 600/459 |

* cited by examiner

SYSTEMS AND METHODS FOR ENSURING COHERENCE BETWEEN MULTIPLE ULTRASOUND TRANSDUCER ARRAYS

CROSS-REFERENCE TO RELATED APPLICATION

This application is a U.S. National Phase Application of PCT/IB2017/000904, filed Jun. 20, 2017, which claims the benefit of and priority to U.S. Provisional Patent Application No. 62/359,922, filed Jul. 8, 2016. The foregoing applications are incorporated herein by reference in their entireties.

FIELD OF THE INVENTION

The present invention relates, generally, to systems and methods involving multiple ultrasound transducers. In particular, various embodiments are directed to maintaining the coherence between multiple ultrasound transducers.

BACKGROUND

Focused ultrasound (i.e., acoustic waves having a frequency greater than about 20 kilohertz) can be used to image or therapeutically treat internal body tissues within a patient. For example, ultrasonic waves may be used to ablate tumors, eliminating the need for the patient to undergo invasive surgery. During tumor ablation, a piezoceramic transducer is placed externally to the patient, but in close proximity to the tissue to be ablated (i.e., the target). The transducer converts an electronic drive signal into mechanical vibrations, resulting in the emission of acoustic waves. The transducer may be shaped so that the waves converge in a focal zone. Alternatively or additionally, the transducer may be formed of a plurality of individually driven transducer elements whose phases can each be controlled independently from one another. Such a "phased-array" transducer facilitates steering the focal zone to different locations by adjusting the relative phases between the transducers. Magnetic resonance imaging (MRI) may be used to visualize the patient and target, and thereby to guide the ultrasound beam.

The effectiveness of ultrasound therapy depends on the properties of the focus (such as the accuracy of the focus location and/or the sharpness and shape of the focal zone). After a focus having the desired properties is created, it is important to maintain it during treatment. This, in turn, depends on persistent coherence among the ultrasound waves that generate the focus. For purposes hereof, two waves are considered to be coherent if they have substantially the same frequency and the difference between their phases is substantially constant.

Conventionally, approaches for ensuring coherence among ultrasound waves emitted from various elements of a single transducer array have been proposed. For example, the geometric locations of the transducer elements with respect to each other and with respect to the transducer body may be measured using, for example, acoustic transmission in the laboratory as part of the manufacturing process. During treatment, the location of the transducer body is determined (e.g., using MRI trackers); as such, the location of each transducer element can be derived from the location of the transducer body. The coherence between the ultrasound waves can be achieved by maintaining the relative locations and/or orientations of the transducer elements with respect to each other.

In some situations, the ultrasound therapy may implement more than one transducer array to provide high ultrasound power and/or sufficient intensity from two distinct acoustic windows. The above-described conventional approach, however, is applicable for maintaining coherence between the ultrasound waves emitted by transducer elements within a transducer array only; it cannot ensure coherence between waves emitted from different transducer arrays.

Accordingly, there is a need for an approach that ensures coherence between ultrasound waves that are emitted from elements of different transducers arrays during treatment.

SUMMARY

Various embodiments of the present invention provide systems and methods for ensuring coherence between ultrasound waves emitted from elements of different transducer arrays by maintaining a constant relative spatial arrangement (e.g., positions and/or orientations) of transducer elements in each transducer array. This may be achieved by limiting the possible geometric locations of the transducer arrays. In various embodiments, two or more transducer arrays are affixed to a connecting structure having predefined constraints. For example, the connecting structure may include an external frame having a limited number of options for positioning the transducer arrays. Locational trackers, such as MRI trackers, may be placed on the transducer arrays to facilitate determining their relative locations with respect to one another and to an anatomic region of interest in a patient's body. This information and the predefined constraints of the connecting structure may together accurately identify the location of the anatomic region of interest and the locations of the transducer elements in the transducer arrays in three-dimensional space. Based on the identified locations of the anatomic region of interest and the transducer elements, an ultrasound transmission configuration (e.g., amplitude, frequency and/or phase) associated with each transducer element may then be computed to ensure that the ultrasound waves emitted by the transducer elements in two or more transducer arrays are coherent at the anatomic region of interest.

Accordingly, in one aspect, the invention pertains to a method for maintaining coherence of waves emitted from multiple ultrasound transducer arrays connected via a connecting frame, each transducer array having multiple transducer elements. In various embodiments, the method includes (a) determining relative locations of the transducer arrays with respect to one another and the connecting frame; (b) determining a location of the connecting frame relative to an anatomic region of interest; (c) determining a spatial arrangement of the transducer elements in each transducer array with respect to the anatomic region of interest based on steps (a) and (b); and (d) based on the determination in step (c), adjusting a transmission configuration (e.g., an amplitude, a frequency and/or a phase) of the transducer elements in the plurality of transducer arrays to achieve a desired focusing property with respect to the anatomic region of interest while maintaining coherence therebetween. In one implementation, the method further includes determining spatial parameters (e.g., locations and/or orientations) of the transducer elements in each transducer array. In addition, step (a) and/or step (b) may be determined using an MR image. In some embodiments, the anatomic region of interest includes a target region for treatment.

Step (a) may include attaching a location tracker to each of the ultrasound transducer arrays and determining relative locations of the locational trackers with respect to one another and the connecting frame. In one embodiment, the method further includes attaching a secondary location tracker to the connecting frame. Step (a) may include determining an orientation angle between two of the transducer arrays from multiple allowed orientation angles. In addition, step (b) may determine a three-dimensional location of the connecting frame relative to the anatomic region of interest, and step (c) may determine a three-dimensional spatial arrangement of the transducer elements in each transducer array with respect to the anatomic region of interest.

In another aspect, the invention relates to a system for maintaining coherence of ultrasound waves during a procedure. In various embodiments, the system includes (a) multiple transducer arrays; (b) multiple retention arms each for receiving one of the transducer arrays; (c) a connecting frame for receiving and mechanically retaining the arms in fixed, known angular relation to each other; and (d) a processor configured to (i) determine relative locations of the transducer arrays with respect to one another and the connecting frame; (ii) determine a location of the connecting frame relative to an anatomic region of interest; (iii) determine a spatial arrangement of the transducer elements in each transducer array with respect to the anatomic region of interest based on the relative locations of the transducer arrays and the location of the connecting frame relative to the anatomic region of interest; and (iv) based on the determined spatial arrangement of the transducer elements in each transducer array with respect to the anatomic region of interest, adjust a transmission configuration (e.g., an amplitude, a frequency and/or a phase) of the transducer elements in the transducer arrays to achieve a desired focusing property with respect to the anatomic region of interest while maintaining coherence therebetween. In one implementation, the processor is further configured to determine spatial parameters (e.g., locations and/or orientations) of the transducer elements in each transducer array.

The system may include multiple locational trackers (e.g., MRI trackers), each in fixed relation to one of the transducer arrays, and a tracking system (e.g., an MR apparatus) for tracking the locational trackers. The processor may be further configured to determine relative locations of the locational trackers with respect to one another and the connecting frame. In addition, the processor may be configured to determine an orientation angle between two of the transducer arrays from multiple allowed orientation angles. In some embodiments, the system further includes an MR apparatus. The relative locations of the transducer arrays with respect to one another and to the connecting frame and/or the location of the connecting frame relative to the anatomic region of interest may then be determined using an MR image. In one implementation, the anatomic region of interest includes a target region for treatment.

In addition, the transducer arrays may be movable along lengths of the retention arms; the system may further include means for mechanically retaining the transducer arrays at selected positions therealong. For example, the transducer arrays may be movable along the lengths of the retention arms only in discrete increments. Alternatively, the transducer arrays may be continuously movable along the lengths of the retention arms. In one embodiment, the connecting frame is configured to provide a series of discrete, angularly displaced mounting locations for the retention arms. In another embodiment, the connecting frame is configured to provide continuous, angularly displaced mounting locations for the retention arms.

As used herein, the term "substantially" means ±10%, and in some embodiments, ±5%. In addition, the term "element" means either an individual transducer in an array or an independently drivable portion of a single transducer. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1:
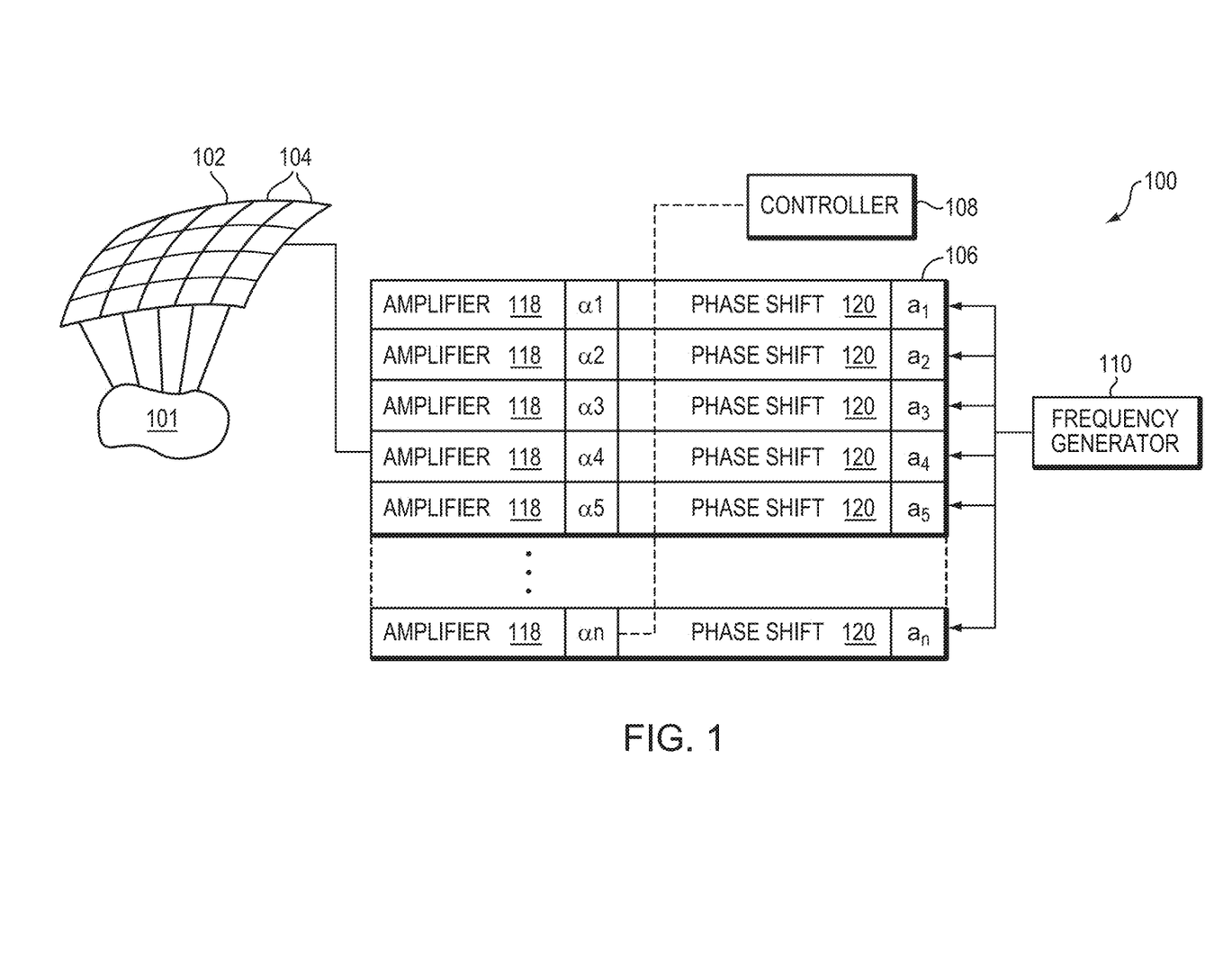
FIG. 1 illustrates an exemplary ultrasound transducer array in accordance with some embodiments of the present invention.

FIG. 1 illustrates an exemplary ultrasound system 100 for generating and delivering a focused acoustic beam to an anatomic region of interest 101 in a patient's body. In various embodiments, the system 100 includes a phased array 102 of transducer elements 104, a beamformer 106 driving the phased array 102, a controller 108 in communication with the beamformer 106, and a frequency generator 110 providing an input electronic signal to the beamformer 106.

The array 102 may have a curved (e.g., spherical or parabolic) shape suitable for placement on the surface of the patient's body, or may include one or more planar or shaped sections. Its dimensions may vary between millimeters and tens of centimeters. The transducer elements 104 of the array 102 may be piezoelectric ceramic elements, and may be mounted in silicone rubber or any other material suitable for damping the mechanical coupling between the elements 104. Piezo-composite materials, or generally any materials capable of converting electrical energy to acoustic energy, may also be used. To assure maximum power transfer to the transducer elements 104, the elements 104 may be configured for electrical resonance at 50Ω, matching input connector impedance.

The transducer elements 104 are separately controllable, i.e., they are each capable of emitting ultrasound waves at amplitudes and/or phases that are independent of the amplitudes and/or phases of the other transducers. In various embodiments, the transducer array 102 is coupled to the beamformer 106, which drives the individual transducer elements 104 so that they collectively produce a focused ultrasonic beam or field. For n transducer elements, the beamformer 106 may contain n driver circuits, each including or consisting of an amplifier 118 and a phase delay circuit 120; each drive circuit drives one of the transducer elements 104. The beamformer 106 receives a radiofrequency (RF) input signal, typically in the range from 0.1 MHz to 10 MHz, from the frequency generator 110, which may, for example, be a Model DS345 generator available from Stanford Research Systems. The input signal may be split into n channels for the n amplifiers 118 and delay circuits 120 of the beamformer 106. In some embodiments, the frequency generator 110 is integrated with the beamformer 106. The radiofrequency generator 110 and the beamformer 106 are configured to drive the individual transducer elements 104 of the transducer array 102 at the same frequency, but at different phases and/or different amplitudes.

The amplification or attenuation factors $\alpha_1$-$\alpha_n$ and the phase shifts $a_1$-$a_n$ imposed by the beamformer 106 serve to transmit and focus ultrasonic energy onto the anatomic region of interest 101, and account for wave distortions induced in the tissue located between the transducer elements 104 and the anatomic region of interest 101. The amplification factors and phase shifts are computed using the controller 108, which may provide the necessary computational functions through software, hardware, firmware, hardwiring, or any combination thereof. For example, the controller 108 may utilize a general-purpose or special-purpose digital data processor programmed with software in a conventional manner, and without undue experimentation, in order to determine the phase shifts and amplification factors necessary to obtain a desired focus or any other desired spatial field patterns at the anatomic region of interest 101.

Figure 2A:
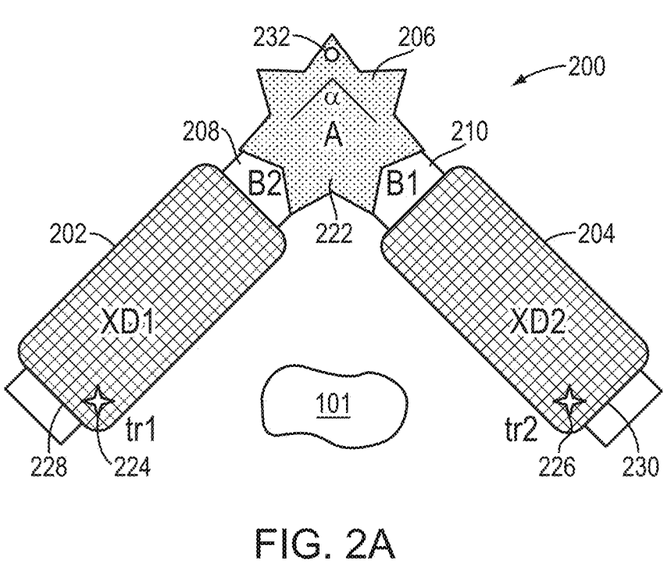
FIGS. 2A and 2B illustrate an exemplary ultrasound system implementing multiple transducer arrays mounted to a connecting frame in accordance with various embodiments of the present invention.

In some embodiments, an ultrasound application may implement more than one transducer array to, for example, provide high ultrasound power and/or sufficient intensity from two distinct acoustic windows. FIG. 2A illustrates a system 200 implementing multiple transducer arrays 202, 204 in accordance with various embodiments. The transducer arrays 202, 204 may be separately driven by the same or different beamformers 106 and/or separately controlled by the same or different controllers 108 in a manner as described above. In various embodiments, the transducer arrays 202, 204 are mounted to a pair of retention arms 208, 210 of a connecting frame 206, which maintains them in fixed relation to each other. For example, the arms 208, 210 may have a discrete number of predetermined position options relative to each other, and the transducer arrays 202, 204 may be movable only along the lengths of the arms 208, 210. The arms 208, 210 may be configured to engage the transducer arrays 202, 204 using any suitable means. For example, referring to FIG. 2B, each of the arms 208, 210 may include a retainer 212 having geometry complementary to the geometry of the transducer arrays 202, 204 for engaging thereto. In one embodiment, the retainers 212 (and thereby the transducer arrays 202, 204) can move along the length of the arms (i.e., x direction) only in discrete increments (e.g., every 10 cm). This may be achieved by utilizing a locking mechanism 216 (e.g., a releasable catch). For example, each of the arms 208, 210 may include multiple slots 218 along the lengths thereof. Each of the retainers 212 may include one or more spring-loaded buttons 220 for engaging one or more slot 218 in the arms 208, 210; the elastic force exerted by the spring may then prevent disengagement of the button 220 from the slot 218. It should be understood, however, that the depicted configurations of the locking mechanism 216 and/or the configurations of engagement of the transducer arrays 202, 204 to the retention arms 208, 210 are for illustration only, and the present invention is not limited to such configurations; one of ordinary skill in the art will understand that any variations are possible and are thus within the scope of the present invention. For example, the retainers 212 may include slidable T members for engaging the slots 218. In addition, the retainers 212 may be operated by an actuation mechanism (e.g., a pump) that is programmable by the controller 108; movement of the transducer arrays 202, 204 along the arms 208, 210 may then be automatically adjusted and computed during the ultrasound procedure.

Figure 2B:
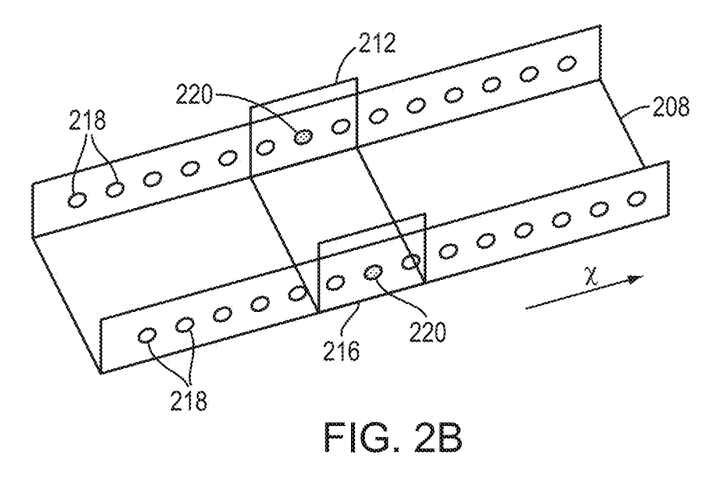

The distance between two consecutive slots 218 in the retention arms 208, 210 defines a minimal increment that the transducer arrays 202, 204 can move along the length thereof; the shorter the distance is, the more locations along the arms 208, 210 that the transducer arrays 202, 204 can be placed. In one embodiment, the slots 218 are sufficiently close to one another (e.g., every 1 cm), the transducer arrays 202, 204 can then be nearly placed anywhere along the arms 208, 210.

Referring again to FIG. 2A, in various embodiments, the arms 208, 210 are coupled to a connector 222 of the connecting frame 206 using any suitable means (e.g., the engaging means as described above). The connector 222 offers a series of discrete, angularly displaced mounting locations for the arms 208, 210 with an angle α between these locations. The number of discrete locations is less important to the operation of the invention than their fixed and desirably equal angular displacements. For example, the angle α may be changed only by a predetermined discrete increment (e.g., 10°). Alternatively, if desired, the discrete angular increment may be sufficiently small (e.g., 1°) to allow nearly continuous angular displacement options from 0° to nearly 360° between the arms 208, 210. Again, the discrete or continuous angular displacement may be achieved using any suitable means (e.g., the locking mechanism and/or actuation mechanism as described above) that is readily available or can be implemented without undue experimentation.

In various embodiments, a pair of locational trackers 224, 226 are attached to the transducer arrays 202, 204, respectively, with fixed positions and/or orientations relative thereto. The locational trackers 224, 226 may be placed in locations that readily facilitate detection and localization with respect to each other and to the anatomic region of interest 101. In one embodiment, the locational trackers 224, 226 are placed on the external edges 228, 230 of the transducer arrays 202, 204, respectively, this configuration maximizes the Euclidean distance between the trackers 224, 226 and, therefore, the ease of resolving the angle α between the two arms 208, 210 as explained below. It should be understood, however, that the locational trackers 224, 226, may be attached to any portion of the transducer arrays 202, 204 or the frame arms 208, 210 so long as the angle α between the two transducer arrays 102, 104 can be resolved. It should also be understood that a larger number of the locational trackers may increase the accuracy (i.e., the resolution) in determining the positions and orientations of the transducer arrays 202, 204. In one implementation, three location trackers 224, 226, 232 are used, each attaching to a transducer array, a frame arm, and/or the connector 222; this may advantageously provide three-dimensional locational information of the connecting frame (and/or transducer arrays) relative to the anatomic region of interest 101.

Figure 3:
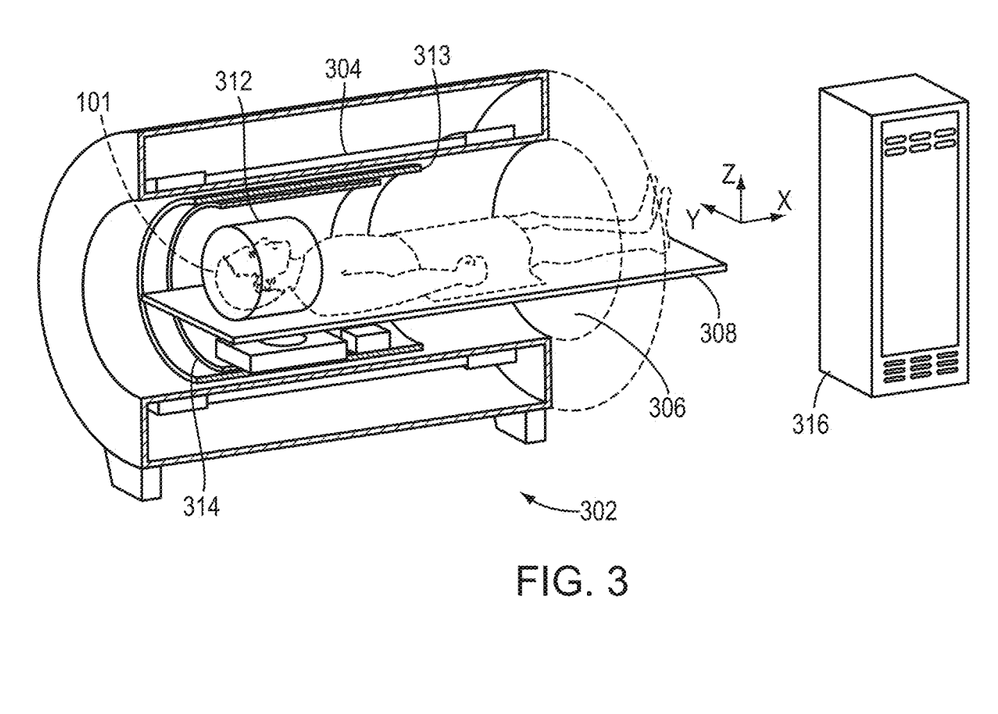
FIG. 3 illustrates an exemplary tracker-tracking system implementing an MRI apparatus in accordance with various embodiments of the present invention.

In one embodiment, the locational trackers 224, 226 are MRI trackers that can be tracked by MR imaging. FIG. 3 illustrates an exemplary MRI apparatus 302. The apparatus 302 may include a cylindrical electromagnet 304, which generates the requisite static magnetic field within a bore 306 of the electromagnet 304. During medical procedures, a patient is placed inside the bore 306 on a movable support table 308. The anatomic region of interest 101 may be positioned within an imaging region 312 wherein the electromagnet 304 generates a substantially homogeneous field. A set of cylindrical magnetic field gradient coils 313 may also be provided within the bore 306 and surrounding the patient. The gradient coils 313 generate magnetic field gradients of predetermined magnitudes, at predetermined times, and in three mutually orthogonal directions. With the field gradients, different spatial locations can be associated with different precession frequencies, thereby giving an MR image its spatial resolution. An RF transmitter coil 314 surrounding the imaging region 312 emits RF pulses into the imaging region 312 to cause the patient's tissues to emit magnetic-resonance (MR) response signals. Raw MR response signals are sensed by the RF coil 314 and passed to an MR controller 316 that then computes an MR image, which may be displayed to the user. Alternatively, separate MR transmitter and receiver coils may be used.

The MRI controller 316 may control the pulse sequence, i.e., the relative timing and strengths of the magnetic field gradients and the RF excitation pulses and response detection periods. The MR response signals are amplified, conditioned, and digitized into raw data using a conventional image-processing system, and further transformed into arrays of image data by methods known to those of ordinary skill in the art. Based on the image data, the location of the anatomic region of interest 101 as well as the locations of the trackers 224, 226, are identified. The image-processing system may be part of the MRI controller 216, or may be a separate device (e.g., a general-purpose computer containing image-processing software) in communication with the MRI controller 216.

In various embodiments, information of the identified locations of the anatomic region of interest 101 and the trackers 224, 226 together with all allowed movements of the frame arms 208, 210 (which are discrete and can be known in advance based on, for example, the default setting or prior measurements as described above) can be used to accurately determine the location and/or orientation of each transducer element of the transducer arrays 202, 204 relative to the anatomic region of interest 101 as further described below. This approach may provide more accurate and efficient determination of the positions of the elements than separately performing position measurement on each transducer element.

Figure 4:
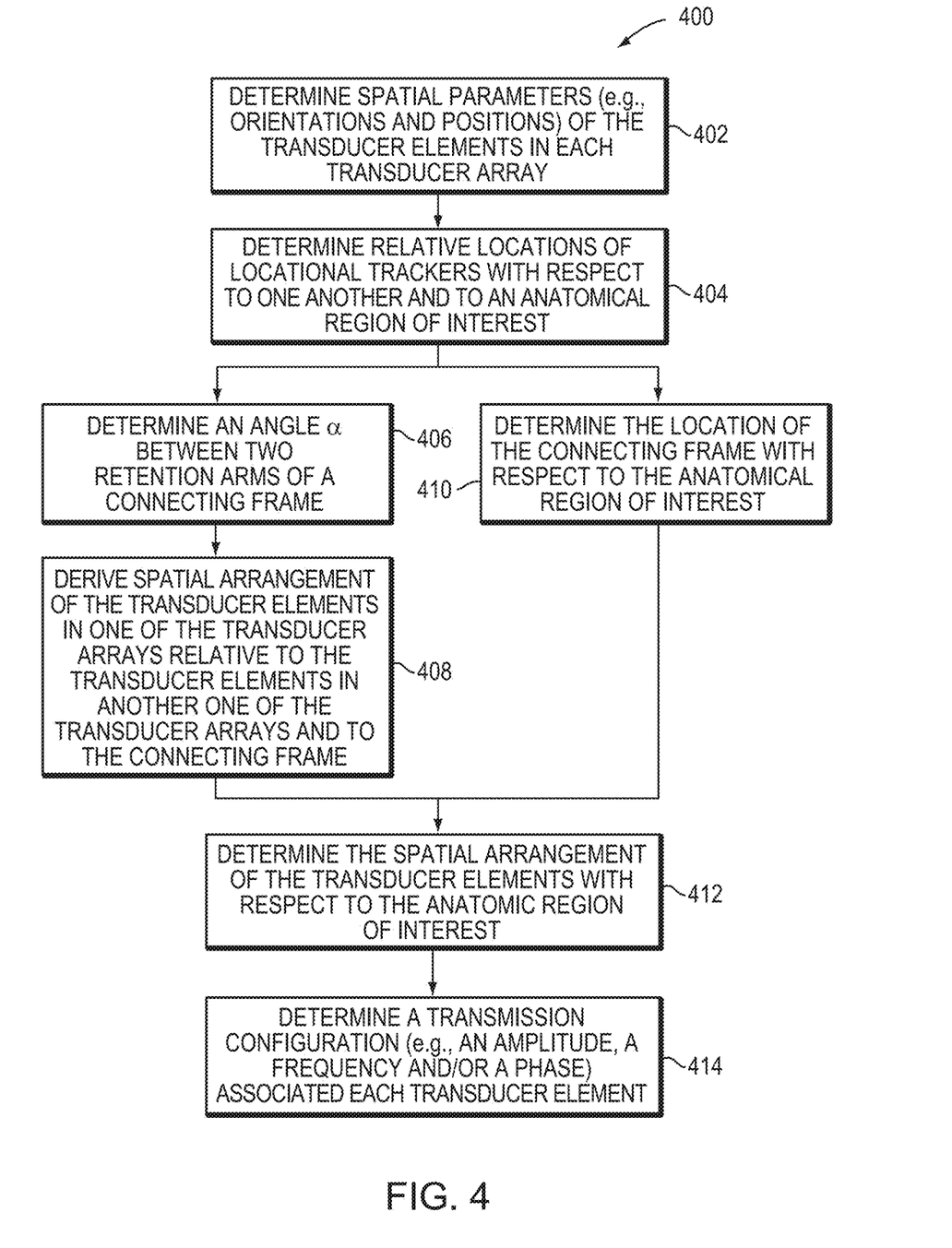
FIG. 4 is a flow chart illustrating an approach for ensuring coherence between ultrasound waves emitted from multiple transducer arrays in accordance with various embodiments of the present invention.

FIG. 4 is a flow chart illustrating an exemplary approach 400 for determining the relative spatial arrangement (e.g., locations and/or orientations) of the transducer elements within each transducer array, and with respect to different transducer arrays and an anatomic region of interest via the use of the connecting frame 206 and locational trackers 224, 226. In a first step 402, spatial parameters, such as the orientations and positions, characterizing transducer elements 104 in each transducer array 202, 204 are obtained using any suitable approach or may be known in advance. For example, each transducer element 104 may emit a pulse towards a sensor (not shown) located at the focus or other position; the distance between each transducer element and the sensor may be determined based on the time of flight. The actual location and/or orientation of each transducer element within each transducer array, in any desired coordinate system (e.g., the coordinate system of the room), can be determined based on this determined distance and the location of the sensor. Alternatively, the orientations and locations of the transducer elements may be determined based on the default design of the transducer arrays and/or MRI images acquired during ultrasound sonications. For example, because the shape of the transducer arrays 202, 204 and the orientations and positions of the transducer elements 104 are generally designed based on the surface of the patient's body to which the transducer arrays are attached, the spatial parameters of each element 104 may be obtained from the default design. In some embodiments, the transducer elements 104 move and/or shift from their expected designed orientations and/or locations during manufacturing, use and repair and/or as a result of the elements 104 being deformed by heat. Various known approaches may be applied to determine the movements and/or shifts for correction; one suitable approach is described in U.S. Pat. No. 7,535,794, the entire disclosure of which is incorporated herein by reference.

In a second step 404, the relative locations of the trackers 224, 226 with respect to one another and/or to the anatomic region of interest 101 are determined using any suitable approach. For example, the trackers 224, 226 may be MRI trackers, and an MRI measurement may be performed to determine the locations of the trackers 224, 226 on the connecting frame 206 and/or relative to an anatomic object (which may be imaged by the MR system) in the anatomic region 101. Based on the determined tracker locations and the allowed angle values available on the connector 222 of the connecting frame 106, the angle α between the two arms 208, 210 upon which the locational trackers 224, 226 are placed may be determined geometrically (in a third step 406); that is, because the number of possible angles (and possibly also the transducer positions along the arms) is constrained, a solution is fully determined using the tracker locations. Alternatively, in some embodiments, an additional locational tracker 232 is attached to the connector 222 connecting the two arms 208, 210. Again, the locations of the three trackers 224, 226, 232 can be identified using any suitable approach (e.g., MRI imaging) as described in connection with step 404; the use of three trackers allows the number of available arm angles and transducer positions along the arms to be increased without making the solution underdetermined.

In a fourth step 408, the relative spatial arrangement (e.g., orientations and positions) of the transducer elements 104 in one of the transducer arrays 202, 204 with respect to the transducer elements in another one of the transducer arrays 202, 204 and with respect to the connecting frame 106 may be derived as a function of the (determined) angle α based on the spatial arrangement of the transducer elements 104 obtained in step 402 and the angle α determined in step 406. In a fifth step 410, the relative location of the anatomic region of interest 101 to the connecting frame 106 to which the transducer arrays 202, 204 are attached is determined based on the locations of the trackers 224, 226 with respect to the anatomic region of interest 101, which was determined in step 404. In a sixth step 412, the spatial parameters of the transducer elements obtained in step 408 and the location of connecting frame 206 determined in step 410 are used together to determine the spatial arrangement of the transducer elements with respect to the anatomic region of interest 101. Based on the determined spatial arrangement of the transducer elements with respect to the anatomic region of interest 101, a transmission configuration (e.g., an amplitude, a frequency and/or a phase) associated with each transducer element may then be computed to ensure that the ultrasound waves emitted by the elements 104 of the transducer arrays 202, 204 are coherent at the anatomic region of interest 101 during treatment (in a seventh step 414). Accordingly, various embodiments of the present invention employ a simple configuration—locational trackers 224, 226 and a connecting frame 206 having predefined constraints—to advantageously allow multiple transducer arrays to be implemented in an ultrasound system for providing high ultrasound power and/or sufficient intensity at the anatomic region of interest 101 while ensuring coherence between the ultrasound waves emitted therefrom.

During treatment, due to movement, a change in the size of the anatomic region of interest 101 and/or other changes, the positions and/or orientations of the transducer elements may require adjustment in order to achieve a desired focusing quality at a desired location. To ensure the coherence of ultrasound waves emitted from multiple transducer arrays during the adjustment, the transducer arrays may be adjusted collaboratively based on the spatial arrangement of the transducer elements with respect to one another and with respect to the anatomic region of interest 101 obtained using the approach 400. For example, a simple adjustment may involve changing the orientation and/or location of the connecting frame 206 with respect to the anatomic region of interest 101 while maintaining the relative positions and orientations of the transducer elements attached thereon unchanged. Alternatively, a more complex adjustment involving movements of the transducer arrays 202, 204 along the length of the retention arms 208, 210 in the connecting frame 206 and/or change in the angle α between the transducer arrays 202, 204 may be implemented to ensure that a focus is generated at the desired location (i.e., at the anatomic region of interest) with a satisfactory quality. The relative spatial arrangement of the transducer elements with respect to different transducer arrays and to the anatomic region of interest 101 after the adjustment may be re-determined in accordance with the approaches described above. Therefore, the present invention advantageously provides an approach to ensure coherence of ultrasound waves emitted from multiple transducer arrays.

In general, functionality for determining the relative spatial arrangement (e.g., orientations and/or locations) of the transducer elements in multiple transducer arrays with respect to the anatomic region of interest, including, determining the spatial arrangement (e.g., orientations and/or locations) of the transducer elements within each transducer array, analyzing imaging data of the anatomic region of interest and locational trackers acquired using an imager, determining the relative locations of the anatomic region of interest with respect to the locational trackers, determining an angle α between two arms of a connecting frame upon which the locational trackers are placed, computing the relative spatial arrangement of the transducer elements in one of the transducer arrays with respect to the transducer elements in another one of the transducer arrays and with respect to the connecting frame, determining the relative location of the anatomic region of interest to the connecting frame, determining the spatial arrangement of the transducer elements with respect to the anatomic region of interest, and computing a transmission configuration (e.g., an amplitude, a frequency and/or a phase) associated each transducer element of the transducer arrays so as to ensure coherence between ultrasound waves emitted therefrom, as described above, whether integrated within a controller of the MRI apparatus, and/or the ultrasound system, or provided by a separate external controller or other computational entity or entities, may be structured in one or more modules implemented in hardware, software, or a combination of both. For embodiments in which the functions are provided as one or more software programs, the programs may be written in any of a number of high level languages such as FORTRAN, PASCAL, JAVA, C, C++, C #, BASIC, various scripting languages, and/or HTML. Additionally, the software can be implemented in an assembly language directed to the microprocessor resident on a target computer (e.g., the controller); for example, the software may be implemented in Intel 80×86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

In addition, the term "controller" used herein broadly includes all necessary hardware components and/or software modules utilized to perform any functionality as described above; the controller may include multiple hardware components and/or software modules and the functionality can be spread among different components and/or modules.

Certain embodiments of the present invention are described above. It is, however, expressly noted that the present invention is not limited to those embodiments; rather, additions and modifications to what is expressly described herein are also included within the scope of the invention. For example, imaging methods other than MRI may be used to track the locational tracker and anatomic region of interest.

What is claimed is:

1. A system for maintaining coherence of ultrasound waves during a procedure, the system comprising:
    (a) a plurality of transducer arrays, each transducer array comprising a plurality of transducer elements;
    (b) a plurality of retention arms each for receiving one of the transducer arrays;
    (c) a connecting frame for receiving and mechanically retaining the arms in fixed, known angular relation to each other, wherein the connecting frame is configured to provide a finite series of allowed, angularly displaced mounting locations for the retention arms; and
    (d) a processor configured to:
        (i) determine relative locations of the plurality of transducer arrays with respect to one another and the connecting frame;
        (ii) determine a location of the connecting frame relative to an anatomic region of interest;
        (iii) thereafter, determine a spatial arrangement of the transducer elements in each transducer array with respect to the anatomic region of interest based on the relative locations of the transducer arrays and the location of the connecting frame relative to the anatomic region of interest; and
        (iv) based on the determined spatial arrangement of the transducer elements in each transducer array with respect to the anatomic region of interest, adjust a transmission configuration of the transducer elements in the plurality of transducer arrays to achieve a desired focusing property with respect to the anatomic region of interest while maintaining coherence therebetween.

2. The system of claim 1, wherein the processor is further configured to determine spatial parameters of the plurality of transducer elements in each of the plurality of transducer arrays.

3. The system of claim 2, wherein the spatial parameters comprise at least one of locations or orientations of the plurality of transducer elements.

4. The system of claim 1, further comprising a plurality of locational trackers, each in fixed relation to one of the plurality of transducer arrays, and a tracking system for tracking the plurality of locational trackers.

5. The system of claim 4, wherein the processor is configured to determine relative locations of the plurality of locational trackers with respect to one another and the connecting frame.

6. The system of claim 5, wherein the processor is configured to determine an orientation angle between two of the plurality of transducer arrays from a plurality of allowed orientation angles, wherein the plurality of allowed orientation angles are based off of the finite series of allowed angularly displaced mounting locations.

7. The system of claim 4, wherein the plurality of locational trackers comprise MRI trackers and the tracking system comprises an MR apparatus.

8. The system of claim 1, further comprising an MR apparatus, wherein the relative locations of the plurality of transducer arrays with respect to one another and to the connecting frame are determined using an MR image.

9. The system of claim 1, further comprising an MR apparatus, wherein the location of the connecting frame relative to the anatomic region of interest is determined using an MR image.

10. The system of claim 1, wherein the anatomic region of interest comprises a target region for treatment.

11. The system of claim 1, wherein the transmission configuration comprises at least one of an amplitude, a frequency or a phase associated with each of the transducer elements.

12. The system of claim 1, wherein the plurality of transducer arrays are movable along lengths of the plurality of retention arms, and further comprising means for mechanically retaining the plurality of transducer arrays at selected positions therealong.

13. The system of claim 12, wherein the plurality of transducer arrays are movable along the lengths of the retention arms only in discrete increments.

14. The system of claim 12, wherein the plurality of transducer arrays are continuously movable along the lengths of the retention arms.

* * * * *